United States Patent [19]

Hoepp et al.

[11] Patent Number: 5,705,706

[45] Date of Patent: Jan. 6, 1998

[54] PROCESS FOR THE PRODUCTION OF 2-(ALKOXYMETHYL)ACROLEIN

[75] Inventors: Mathias Hoepp, Biebergemuend; Klaus Koehler, Hainburg; Dietrich Arntz, Oberursel, all of Germany

[73] Assignee: Degussa Aktiengesellschaft, Frankfurt am Main, Germany

[21] Appl. No.: 681,509

[22] Filed: Jul. 23, 1996

[30] Foreign Application Priority Data

Aug. 8, 1995 [DE] Germany .......... 195 29 125.5

[51] Int. Cl.$^6$ ............ C07C 45/61
[52] U.S. Cl. .......... 568/460; 568/449; 568/420
[58] Field of Search ............ 568/460, 449, 568/420

[56] References Cited

U.S. PATENT DOCUMENTS 5,177,266  1/1993  Strong .......... 568/460
5,281,713  1/1994  Strong .......... 546/179

*Primary Examiner*—Gary Geist
*Assistant Examiner*—S. Padmanabhan
*Attorney, Agent, or Firm*—Beveridge, DeGrandi, Weilacher & Young, L.L.P.

[57] ABSTRACT

2-(Alkoxymethyl)acrolein of the formula

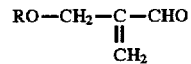

is produced from acrolein, an alcohol ROH and formaldehyde, in one step, with a good yield being obtained. The acrolein is reacted with a substantially equimolar quantity of a source of formaldehyde in the presence of at least an equimolar quantity of the alcohol ROH and a catalytic quantity of a catalyst system based on a secondary amine and a mineral acid at a pH value of the reaction mixture in the range of 1 to less than 7.

24 Claims, No Drawings

PROCESS FOR THE PRODUCTION OF 2-(ALKOXYMETHYL)ACROLEIN

INTRODUCTION AND BACKGROUND

The present invention relates to a process for the production of 2-(alkoxymethyl)acrolein. The process is based on the reaction of acrolein with the appropriate alcohol and formaldehyde in the presence of a catalyst.

A process for the production of 2-(alkoxymethyl)acrolein is described in U.S. Pat. Nos. 5,281,713 and 5,177,266. The processes described in these documents involve reactions carried out in two steps: in a first step a $C_1$ to $C_6$ alcohol is reacted with at least an equimolar quantity of acrolein in the presence of a mineral acid and a catalytic quantity of a trisubstituted amine in a solvent; the solvent is water or a mixture of water and a water-soluble organic solvent. The reaction product of this first step, 3-alkoxypropionaldehyde, is reacted in the second step with formaldehyde in an aqueous reaction medium in the presence of a mineral acid and a catalytic quantity of a disubstituted amine. The 2-(alkoxymethyl)acrolein formed is separated off from the aqueous phase by means of extraction and the extract is recovered by distillation.

The above process has a series of disadvantages: the yield is low; for 2-(methoxymethyl)acrolein, which is particularly important for further processing into herbicides, the yield is given as 44%. In addition, the space-time yield of the process is low since the formation of the intermediate step itself requires a reaction time of several hours and in addition the recovery of the reaction mixture by extraction requires suitable extraction apparatus. Finally, an organic solvent which is substantially insoluble in water is additionally necessary for the extraction.

Therefore an object of the present invention is to improves the known process in terms of the yield and preferably also the space-time yield. A further object is aimed at reducing the overall quantity of apparatus required and avoiding the need for a solvent for the extraction.

SUMMARY OF THE INVENTION

In achieving the above and other objects, one feature of the invention is a process for the production of 2-(alkoxymethyl)acrolein of the general formula I

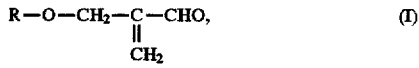

(I)

wherein R signifies an alkyl group with 1 to 6 C atoms or an alkoxyalkyl group with a total of 3 to 6 C atoms.

The process is carried out by reacting acrolein, an alcohol of the formula ROH, wherein R has the same meaning as above, and a source of formaldehyde in which the acrolein is reacted with a substantially equimolar quantity of a source of formaldehyde in the presence of at least an equimolar quantity of the alcohol ROH and a catalytic quantity of a catalyst system based on a secondary amine and a mineral acid. No additional catalyst is required. The pH value of the reaction mixture is in the range of 1 to less than 7. The process according to the invention is a one-step process which avoids the need for using an organic solvent for purposes of extraction.

DETAILED DESCRIPTION OF INVENTION

According to more detailed aspects of the invention when carrying out the process it is preferred to utilize a primary or secondary alcohol with 1 to 4 carbon atoms and polymeric formaldehyde as the source of formaldehyde. The temperature of the reaction is sufficient for the reaction to proceed and generally is in the range of 20° to 100° C. Although the pH of the reaction system is generally in the range of 1 to less than 7, it is preferred to be in the range of 3 to 6.5. Proportions of acrolein and alcohol are not narrowly critical. For example, a molar ratio of acrolein to alcohol can range from 1 to 2 up to 1 to 10.

The R group in the 2-(alkoxymethyl)acrolein denotes an alkyl group with 1 to 6 C atoms, wherein the alkyl group may be linear or branched. The C atom adjacent to the O atom of the alcohol of formula ROH to be used is primary or secondary, but not generally tertiary. R denotes particularly preferably methyl, ethyl, n-propyl, isopropyl, n-butyl and isobutyl. R may also denote a cyclic alkyl, such as cyclopentyl and cyclohexyl. Where R is an alkoxyalkyl group with a total of 3 to 6 C atoms, the alkylene group contains 2 to 5 C atoms and the alkoxy group 1 to 3 C atoms.

Surprisingly, it was found that the separate production of the intermediate compound 3-alkoxypropionaldehyde is not necessary. It is sufficient to produce the intermediate step in situ and to further react it with formaldehyde immediately without separation. The same catalyst system, a combination of a secondary amine and a mineral acid, as the sole catalyst, is used for both reactions, i.e. the alcohol addition to acrolein and the Mannich reaction, which take place side by side in the process according to the invention. Thus, it will be noted that in the present invention, unlike the prior art, the reaction proceeds with one catalyst in a single step with no separation of the intermediate 3-alkoxypropionaldehyde, there being no other catalyst used in the reaction.

The secondary amine of the catalyst system is an amine of the general formula $R^1R^2NH$, wherein $R^1$ and $R^2$ are linear or branched alkyl with 1 to 6 C atoms, preferably 2 to 4 and in particular 4 C atoms, but not tert-alkyl. $R^1$ and $R^2$ may together represent an alkylene group with 4 or 5 C atoms. Sulphuric acid, phosphoric acid, hydrochloric acid and nitric acid in particular may be considered as the mineral acid of the catalyst system, but sulphuric acid is particularly preferred. The quantity of secondary amine and mineral acid used is generally in the range of between 5 and 50 mmol, preferably between 20 and 30 mmol, per mol acrolein. The quantitative ratio between the secondary amine and the mineral acid is selected such that a pH value in the range of 1 to less than 7 results in the reaction mixture of the alcohol the source of formaldehyde and acrolein. The pH value is preferably between 3 and 6.5.

Based on acrolein, the alcohol is used in at least an equimolar ratio; however a molar ratio of acrolein to alcohol of 1 to 2 up to 1 to 10 is preferred. A molar ratio of acrolein to alcohol in the range of from 1 to 4 up to 1 to 8 is particularly preferred.

Suitable sources of formaldehyde are an aqueous or alcoholic formaldehyde solution, but oligomeric or polymeric formaldehyde as is generally used commercially is preferred; paraformaldehyde is particularly preferred. Acetals of formaldehyde which are capable of depolymerization under the reaction conditions may also be considered as a further source of formaldehyde, the alcohol component of the acetal being identical with the alcohol which is a component of the 2-(alkoxymethyl)-acrolein to be produced.

Acrolein and the source of formaldehyde are used in a substantially equimolar quantity. The term "substantially" here is intended to mean that the formaldehyde resulting from the source of formaldehyde may be present in a slightly smaller quantity than acrolein, up to approximately 10 mol %, but desirably in a slight excess, up to 30 mol %, preferably 5 to 15 mol %.

The process according to the invention is usually carried out at temperatures in the range of between 0° and 120° C., but a temperature in the range of between 20° and 100° C. is preferred and a temperature in the range of between 40° and 100° C. is particularly preferred.

According to a preferred embodiment of the process according to the invention the source of formaldehyde, preferably an anhydrous source of formaldehyde and particularly preferably paraformaldehyde, is first added to a mixture of the alcohol to be reacted and the catalyst system. This mixture, which preferably has a pH value of 3 to 6.5, is brought up to the desired reaction temperature, preferably 40° to 100° C. Acrolein is then incorporated in such a way that the reaction mixture never contains a very large concentration of 3-alkoxypropionaldehyde, but this reacts immediately to the desired 2-(alkoxymethyl)acrolein. The content of 3-alkoxypropionaldehyde in the reaction mixture is generally clearly below 20 mol %, usually clearly below 10 mol %, based on the acrolein incorporated. Under the conditions mentioned, the reaction is already completed when the addition of acrolein is completed.

The reaction mixture may be recovered directly by distillation. It is also possible to separate the reaction mixture from the catalyst first by a rapid distillation using a thin-layer evaporator. Excess alcohol is recovered by subsequent rectification and the desired 2-(alkoxymethyl)acrolein is then isolated. In the case of 2-(methoxymethyl)acrolein this is isolated as an azeotropic mixture with water which is present. This mixture may be used directly for further reactions in which water is not a problem.

The distillate receiver is advantageously stabilized with small quantities of acid, generally 0.1 to 1.0 wt. % phosphoric or citric acid, in order to rule out polymerization of the product by traces of amine distilled with the product.

If desired, the azeotropic mixture may be dehydrated by means of conventional techniques, for example azeotropic dehydration or by pervaporation, and the pure 2-(alkoxymethyl)acrolein may thus be obtained.

Substantial advantages of the process are:
the fact that the reaction is carried out in one step
a reduction in the quantity of apparatus used
the ability to dispense with an organic solvent since the extraction step is omitted
a higher space-time yield compared with known processes
a higher yield of 2-(alkoxymethyl)acrolein in the preferred embodiment.

EXAMPLE 1

Production of 2-(methoxymethyl)acrolein

Paraformaldehyde (33 g, 1.1 mol) is suspended in a mixture consisting of acrolein (58 g, 1 mol), methanol (224 g, 7 mol), dibutylamine (6.8 g, 0.029 mol) and sulphuric acid (2.5 g, 0.024 mol). The suspension is heated for 2.5 h with reflux until the paraformaldehyde has largely gone into solution and reacted.

Distillation is then carried out directly. The excess methanol is first distilled off under normal pressure, and then the product is obtained in a mixture with water and methanol under a pressure of 100 mbar and at a temperature of 34° to 46° C. The product is stabilized with 0.5 g of phosphoric acid. The content is determined by GC analysis. 90 g of product is obtained with a content of 50% 2-(methoxymethyl)acrolein; yield=45%.

EXAMPLE 2

Production of 2-(methoxymethyl)acrolein

Paraformaldehyde (33 g, 1.1 mol) is suspended in a solution of dibutylamine (6.8 g, 0.029 mol) and sulphuric acid (2.5 g, 0.024 mol) in methanol (224 g, 7 mol). The suspension is heated with reflux; acrolein (58 g, 1 mol) is dropped in continuously over a period of 2 h. Once the addition is completed, heating is continued for a further 5 minutes with reflux.

Distillation is then carried out directly. The excess methanol is first distilled off under normal pressure, and then the product is obtained in a mixture with water and a small quantity of methanol under a pressure of 100 mbar and at a temperature of 40° to 62° C. The distillate is stabilized with a small quantity of phosphoric acid and hydroquinone. The content is determined by GC analysis. 117 g of product is obtained with a content of 64% 2-(methoxymethyl)acrolein; yield=75%.

EXAMPLE 3

Production of 2-(methoxymethyl)acrolein

A mixture consisting of acrolein (58 g, 1 mol), methanol (224 g, 7 mol), dibutylamine (6.8 g, 0.029 mol), sulphuric acid (2.5 g, 0.024 mol) and 37% aqueous formaldehyde solution (89 g, 1.1 mol) is heated with reflux for 2.5 h.

Distillation is then carried out directly. The excess methanol is first distilled off under normal pressure, and then the product is obtained in a mixture with water and methanol under a pressure of 100 mbar and at a temperature of 34° to 46° C. The product is stabilized with 0.5 g of phosphoric acid. The content is determined by GC analysis. 97 g of product is obtained with a content of 60% methoxymethylacrolein. Yield=58%.

EXAMPLE 4

Production of 2-(ethoxymethyl)acrolein

The reaction takes place as in example 2, with 7 mol ethanol being used as the alcohol component. After recovery by distillation, 85 g of 2-(ethoxymethyl)acrolein is obtained, corresponding to a yield of 75%.

EXAMPLE 5

Production of 2-(isopropoxymethyl)acrolein

The reaction takes place as in example 2, with 7 mol isopropanol being used as the alcohol component. After recovery by distillation, 87 g of 2-(isopropoxymethyl) acrolein is obtained, corresponding to a yield of 68%.

Further variations and modifications of the invention herein described will be apparent to those skilled in the art from the foregoing and are intended to be encompassed by the claims appended hereto.

German priority application 195 29 125.5 is relied on and incorporated hereby by reference.

We claim:

1. A process for the production of 2-(alkoxymethyl) acrolein of the formula I

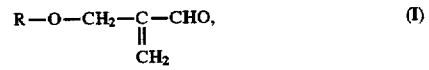

wherein R signifies an alkyl group with 1 to 6 C atoms or an alkoxyalkyl group with a total of 3 to 6 C atoms, comprising reacting acrolein with a substantially equimolar quantity of a source of formaldehyde in the presence of at least an equimolar quantity of an alcohol of the formula ROH, wherein R has the same meaning as above, and a catalytic quantity of a catalyst system which is a secondary amine and a mineral acid at a pH value of the reaction mixture in the range of 1 to less than 7, in a single reaction step without separation of the intermediate 3-alkoxypropionaldehyde.

2. The process according to claim 1, wherein the alcohol is a primary or secondary alcohol with 1 to 4 C atoms.

3. The process according to claim 1, wherein the source of formaldehyde.

4. The process according to claim 2, wherein the source of formaldehyde.

5. The process according to claim 1 the reaction is carried out at a temperature in the range of between 20° and 100° C.

6. The process according to claim 2 the reaction is carried out at a temperature in the range of between 20° and 100° C.

7. The process according to claim 3 the reaction is carried out at a temperature in the range of between 20° and 100° C.

8. The process according to claim 1 wherein the reaction is carried out at a pH, value of the reaction mixture in the range of 3 to 6.5.

9. The process according to claim 2 wherein the reaction is carried out at a pH value of the reaction mixture in the range of 3 to 6.5.

10. The process according to claim 3 wherein the reaction is carried out at a pH value of the reaction mixture in the range of 3 to 6.5.

11. The process according to claim 4 wherein the reaction is carried out at a pH value of the reaction mixture in the range of 3 to 6.5.

12. The process according to claim 1 wherein acrolein and alcohol of the formula ROH are used in the molar ratio of 1 to 2 up to 1 to 10.

13. The process according to claim 2 wherein acrolein and alcohol of the formula ROH are used in the molar ratio of 1 to 2 up to 1 to 10.

14. The process according to claim 3 wherein acrolein and alcohol of the formula ROH are used in the molar ratio of 1 to 2 up to 1 to 10.

15. The process according to claim 4 wherein acrolein and alcohol of the formula ROH are used in the molar ratio of 1 to 2 up to 1 to 10.

16. The process according to claim 5 wherein acrolein and alcohol of the formula ROH are used in the molar ratio of 1 to 2 up to 1 to 10.

17. Process according to claim 1 wherein the source of formaldehyde is first added to a mixture of the alcohol and the catalyst system and is brought to a temperature of reaction and then acrolein is incorporated in such a way that the reaction mixture always contains less than 20 mol % 3-alkoxypropionaldehyde, based on the acrolein incorporated.

18. The process according to claim 17, acrolein is incorporated at a temperature of reaction in the range of 40° to 100° C. at a pH value of 3 to 6.5.

19. The process according to one of claim 18, wherein the reaction mixture is recovered by distillation on completion of the reaction.

20. The process according to claim 1 which is a single step process without separate production of the intermediate 3-alkoxypropionaldehyde.

21. The process according to claim 20 whereby 2-(alkoxymethyl) acrolein is recovered with the use of an organic solvent in an extraction step.

22. The process according to claim 1 wherein acrolein, formaldehyde, alcohol and catalyst system are added together and reacted in a single reaction step.

23. The process according to claim 1 wherein the catalyst system of secondary amine and mineral acid is the only catalyst present in the reaction mixture.

24. The process according to claim 1 wherein no organic solvent is present in the reaction mixture.

* * * * *